United States Patent [19]

Fahim

[11] Patent Number: 5,372,822
[45] Date of Patent: Dec. 13, 1994

[54] CHEMICAL CASTRATION

[76] Inventor: Mostafa S. Fahim, 500 Hulen Dr., Columbia, Mo. 65203

[21] Appl. No.: 206,469

[22] Filed: Mar. 7, 1994

[51] Int. Cl.$^5$ .............................................. A61K 33/30
[52] U.S. Cl. ..................................................... 424/643
[58] Field of Search ......................................... 424/643

[56] References Cited

U.S. PATENT DOCUMENTS

| | | | |
|---|---|---|---|
| 4,156,427 | 5/1979 | Fahim | 128/215 |
| 4,185,618 | 1/1980 | Corey | 128/1 |
| 4,326,523 | 4/1982 | Wolfrom et al. | 128/260 |
| 4,339,438 | 7/1982 | Fahim | 424/145 |
| 4,384,206 | 5/1983 | Bjarno | 250/339 |
| 4,563,428 | 1/1986 | Mortensen | 436/21 |
| 4,610,877 | 9/1986 | Pearson et al. | 424/88 |
| 4,665,064 | 5/1987 | Hider et al. | 514/184 |
| 4,906,563 | 3/1990 | Singh et al. | 435/7 |
| 4,937,234 | 6/1990 | Fahim | 514/53 |
| 4,946,688 | 8/1990 | Fahim | 424/643 |
| 5,070,080 | 12/1991 | Fahim | 514/53 |
| 5,071,658 | 12/1991 | Fahim | 424/643 |
| 5,234,698 | 8/1993 | Fahim | 424/643 |

OTHER PUBLICATIONS

Zinc Treatment for Reduction of Hyperplasia of Prostate, Fahim et al, submitted to American Society for Pharmacology, 1976.
Effects of Lead & Cadmium on Adrenal & Thyroid Functions in Rats, Fahim et al, submitted to American Physiological Society, 1976.
Cadmium and Lead Injection Into Prostate, Khare et al, submitted to American Society of Andrology, 1978.
Chemical Sterilant for Dogs, Fahim et al, Archives of Andrology 9:13-15, Reproductive Health Care, Intl Symposium, Oct. 1982.
Chemical Sterilant for Dogs, Fahim et al, Contraceptive Delivery Systems, vol. 3 No. 3/4, Jul. 1982.
Chemical Sterilant for Pets, Part I: Dogs, Fahim et al, Fertility and Sterility, Mar. 1983, vol. 39, No. 3, Abstract Supplement.

Testicular Zinc Distribution in Zinc Tannate-Injected Testis, Arch. Androl. 12 (2-3), 1984, Abstracts.
Effect of Zinc Tannate on Dog Prostate, Fahim et al, submitted to 5th Forum of International Andrology, Jun. 1987.
Zinc Tannate as a Chemical Sterilant in Cattle, Fahim et al, submitted to XXIII World Veterinary Congress, 1987.
Zinc Tannate as a Chemical Sterilant in Dogs, Fahim et al, submitted to XXIII World Veterinary Congress, 1987.
Effect of Zinc Tannate on Dog Sperm, Fahim et al, submitted to The American Fertility Society Annual Meeting, 1987.
Intraepididymal Injection of Neutralized Zinc Gluconate, Fahim et al, submitted to The American Fertility Society Annual Meeting, 1989.
Intraprostatic Injection of Neutralized Zinc in Rats, Fahim et al, The FASEB Journal, vol. 5, No. 4, Abstracts, Mar. 11, 1991.
Chemical Castration in Prepubertal Dogs, Bouchard et al, submitted to Society for Theriogenology Annual Meeting, 1991.
Chemical Sterilization in Puppies, Bouchard et al, submitted to XXIV World Veterinary Congress, 1991.
Chemical Vasectomy in Sexually Mature Dogs, Fahim et al, submitted to The Americal Fertility Society, 1991.

(List continued on next page.)

*Primary Examiner*—Shep K. Rose
*Attorney, Agent, or Firm*—Grace J. Fishel

[57] ABSTRACT

A method for chemically castrating male pigs in a manner that modulates the production of testosterone and interferes with the enzymatic conversion of testosterone into androstenone by injecting a mineral acetate solution into both testes or epididymides in an amount effective to reduce the pig's serum testosterone level below that of an intact male.

5 Claims, No Drawings

OTHER PUBLICATIONS

Environmental Interaction of Lead and Cadmium on Reproduction, Comm in Chemical Pathology & Pharmacology, vol. 14, No. 4, Aug. 1976.

Effects of Lead and Cadmium on Adrenal and Thyroid Functions in Rats, Comm in Chemical Pathology & Pharmacology, vol. 17, No. 2, Jun. 1977.

Prostatic Cellular Changes after Injection of Cadmium and Lead, Research Comm in Chemical Pathology, vol. 20, No. 2, May 1978.

Effects of Subtoxic Levels of Lead and Cadmium on Urogenital Organs of Male Rats, Archives of Andrology, 4, 357–362, 1980.

Chemical Sterilization in the Male Part I: Rats, Archives of Andrology, 9:261–265, 1982.

Pharmacokinetics of Zinc Tannate after Intratesticular Injection, Archives of Andrology, 13:129–136, 1984.

Value of Intraprostatic Injection of Zinc and Vitamin C, Archives of Andrology, 14:81–87, 1985.

Sterilization of Dogs with Intra-Epididymal Injection of Zinc Arginine, Contraception, 47:107–122, 1993.

Zinc Arginine a 5alpha-reductase inhibitor reduces rat ventral prostate weight, Andrologia 25, 369–375, 1993.

Zinc Tannate as a Chemical Sterilant in Cattle, XXIII World Veterinary Congress, Aug. 16–21, 1987.

Zinc Tannate as a Chemical Sterilant in Dogs, XXIII World Veterinary Congress, Aug. 16–21, 1987.

CHEMICAL CASTRATION

The present invention relates to a process for chemically castrating male pigs in a manner that produces a bigger, leaner animal as compared to barrows while eliminating the unpleasant odor or "boar taint" found in boar meat. It is more humane and does not have the side effects of knife castration (e.g., bleeding, hernia, infection and sometimes death).

BACKGROUND OF THE INVENTION

In most livestock species, it is well documented that intact males out perform, are more efficient and are superior in most carcass traits compared to their castrated counterparts. In swine, Wood and Riley (1982) and Hines et al. (1969) found that boars grew faster than barrows and were more efficient in converting feed to tissue. Additionally, Kuhlers et al. (1976) reported that boars had significantly less backfat and a larger loin eye area than barrows of the same live weight. For this reason in some European countries (e.g., Great Britain, Ireland and Spain) most slaughter pigs are intact males (Walstra, 1984). Yet, with the obvious advantages associated with the production of boars, come the problems that encouraged the development of castration.

The most economically important problem with growing boars for meat production is the unpleasant odor or "boar taint" found in boar meat during cooking. Studies suggest that between 5 and 35 percent of market weight boar carcasses are tainted at a level offensive to consumers (Malmfors and Lundstrom, 1983). Additional concerns with intact male production are increased aggressive behavior, increased rates of down pigs, demands on facilities, separate sex feeding and increased danger to human caretakers.

As discussed previously, the major economic shortcoming of intact male swine production for slaughter is boar taint. This unpleasant odor was first studied by Lerche (1936) who showed the early appearance of the odor coincided with the onset of puberty and disappeared following castration. Patterson (1968) using chromatography-mass-spectrometry isolated 5-alpha-androst-16-en-3-one (androstenone) as a major component of this odor. Shortly afterwards this finding was confirmed and 5-alpha-androst-16-en-3-alpha-ol and 5-alpha-androst-16-en-3-beta-ol were identified as minor contributors (Beery and Sink, 1971; Berry et al., 1971). About the same time another much different compound skatole, which possesses a strong fecal odor, was found to act synergistically with and strengthen the foul odor of androstenone (Vold, 1970; Walstra and Maarse, 1970).

Skatole and androstenone are very unrelated in their production. Androstenone, and other 16 androstenes that are found bound in boar fat, are produced in the testes with pregnenolone as the precursor (Brooks and Pearson, 1989). These compounds are released into the blood via the spermatic vein and are stored in fat (Bonneau and Terqui, 1982). The 5-alpha-androst-16-en-3-one configuration is the predominant storage form because it is the most lipophilic and it is therefore the major component responsible for boar taint (Claus, 1979). During sexual stimulation these steroids can be released back into the bloodstream to travel to the submaxillary gland for use as an important pheromone in saliva (Gower, 1972; Claus, 1979). It is apparent that this storage procedure is also reversible over time because after castration of older males, steroid concentrations in adipose tissue decline (Claus, 1976).

The levels of androstenone found in boar fat vary widely and are affected by age, weight, genetics and stage of sexual maturity (Jonsson and Andresen, 1979; Bonneau, 1981; Willeke, 1980; Walstra, 1984). Additionally, they may be sensitive to external stimuli such as rearing environment or sexual exposure although the literature is somewhat conflicting. As a general rule androstenone production begins increasing slowly when the animal reaches about 70 kg or approximately 4 months of age (Bonneau, 1981). It is also known that the highest incidence of objectionable odor in fat occurs in boars weighing over 95 kg and greater than 5 months of age (Walstra, 1984).

The other component isolated as a major factor in boar taint is skatole. It is produced by lactobacilli in the hindgut of the pig as these microorganisms break down tryptophan (Yokoyama and Carlson, 1979). Skatole concentration can be altered somewhat by diet and is normally found in excess of threshold levels (0.20 ppm) in boars. However, these levels are rarely reached in barrow or gilt fat (Mortensen et al., 1986) even though gut microflora differs only slightly between the sexes. This may indicate a hormonal influence either in the absorption rate of skatole or the rate of storage and degradation once absorbed (Lundstrom et al., 1988).

Moderately high to high correlations have been reported between sensory panel scores for boar odor and laboratory analysis for both androstenone and skatole levels in boar fat. Lundstrom et al. (1988) reported a correlation of $r=0.53$ for androstenone concentration compared with sensory panel scores for boar odor and a slightly higher correlation (0.65) for skatole level compared to the same sensory scores. Additionally, a smaller (0.32) correlation was reported between skatole and androstenone concentrations. Hansson et al. (1980) reported a coefficient of determination of 36 percent for boar odor by using androstenone alone; however, when skatole values were added to the model an r-squared value of 0.5 was achieved. Undoubtedly both compounds are important in determining boar odor levels and their interaction is very likely.

Historically, surgical castration has been the choice of most swine producers to deal with boar taint. Though relatively easy, inexpensive and very effective it is not the perfect solution. The testes of a pig is highly vascular and filled with nerves and for these reasons pigs are usually castrated at an early age and knife castration is not done on mature boars. Hence besides reducing growth and carcass quality, there are other risks involved in surgical castration: infection, severe herniation and killing or stunting animals due to large losses of blood during the operation or after re-injury by other animals.

Recently other methods have been tried to overcome the problems associated with surgical castration. For example, intact males have been treated with progestagen either through an implant or in the diet (Berger et al., 1981; Kluber et al., 1988). Immunization of boars against one of the compounds responsible for boar taint has also been tried. (Williamson et al., 1985; Brooks et al., 1986). Both of these methods have serious problems: hormonal treatment must be repeated several times and is not acceptable in swine for human consumption in some cultures. Immunization is not uniformly effective in all animals and there is some risk that cross-reacting antibodies will be induced causing undesired side effects.

In view of the problems with surgical, hormonal and immunocastration, there is a continuing need for an improved method of castration that controls boar taint, preferably without affecting growth and carcass quality. The present invention relates to a method of chemical castration and accomplishes those goals.

By way of review, there are two approaches to chemical castration, the first being to inject a sclerotic agent into the vas deferens of an intact male causing an occlusion in the duct blocking the transport of sperm and rendering the animal infertile. This type of chemical sterilization induces infertility but does not reduce the production of testosterone or other testicular steroids responsible for boar taint and male aggressiveness. Many compounds have been shown effective for this purpose: 10 percent silver nitrate or 3 percent formalin (Pineda et al., 1976); 95 percent ethanol (Freeman and Coffee, 1973); dondren (Bierschwal and Ebert, 1961); and quinacrine (Malaviya et al., 1974).

The second type of chemical castration and the type employed in the present invention involves an agent responsible for tissue modification and subsequent disruption of testicular function. The particular effect observed depends on the chemical and concentration injected, species, maturity of the animal and so forth. U.S. Pat. Nos. 4,156,427 and 4,339,438 to Fahim describe the use of zinc tannate as a chemical sterilant. Applicant's early data were collected on sexually mature Holzman strain rats injected with zinc tannate. Zinc tannate was also tried on cattle but caused difficulty in walking. The extent of discomfort in movement did not appear to be dose dependent and went away within 2-3 days after injection. No loss of appetite or reduction in feed consumption was reported. With pigs, however, and particularly with baby pigs, applicant has found that zinc tannate is neurotoxic when injected into the testes causing convulsions, loss of coordination and sometimes death.

Because of the difficulty in walking problem associated with the injection of zinc tannate, lactic acid and other acidic compounds, applicant developed a neutral chemical sterilant that can be injected without causing discomfort. U.S. Pat. No. 5,070,080 to Fahim describes the use of a neutralized solution of a mineral gluconate and amino acid, a typical example of which is zinc arginate. When applicant injected zinc arginate in pigs (see Example 1 below), the boars were sterilized but boar taint was not reduced. Applicant then evaluated other zinc salts, the present invention relating to the discovery that mineral acetate salts are not neurotoxic and, if administered in a proper amount, chemically castrate pigs in a manner that eliminates boar taint without reducing growth and carcass quality.

SUMMARY OF THE INVENTION

In view of the above, it is an object of the present invention to chemically castrate male pigs in a manner that produces a bigger, leaner animal as compared to barrows while eliminating the unpleasant odor or "boar taint" found in boar meat. These improvements in the efficiency and rate of lean tissue accretion could have a dramatic impact on the meat supply if applied on an industry wide basis. It is another object to chemically castrate male pigs in a humane manner that does not traumatize them and that can be administered at any age or stage of development. Other objects and features of the invention will be in part apparent and in part pointed out hereinafter.

In accordance with the invention, a method of chemically castrating a male pig in a manner that modulates the production of testosterone and interferes with the enzymatic conversion of testosterone into androstenone is disclosed. The method involves injecting a solution of a mineral acetate such as zinc acetate or calcium acetate into each testes or epididymis in an amount effective to reduce the pig's serum testosterone level as compared to an intact pig. The chemically castrated pig's growth and carcass quality is as good as or better than an intact male and boar taint is reduced.

The invention summarized above comprises the methods hereinafter described, the scope of the invention being indicated by the subjoined claims.

DETAILED DESCRIPTION OF THE INVENTION

In the present invention, the injection of a mineral acetate solution into both testes or epididymides of a male pig changes the vascularity of the testes in a manner that modulates the production of testosterone and interferes with the enzymatic conversion of testosterone into androstenone. Other zinc salts (e.g., zinc arginate) are capable of chemically castrating a pig but they are not effective at inhibiting the production of androstenone and reducing boar taint. Some, such as zinc tannate, are neurotoxic in pigs causing convulsions, difficulty in walking and so forth.

The method can be used on pigs at any stage of development, from one-day old piglets to old boars, and the extent to which testicular function is disrupted can be from completely (i.e., like knife castrates) to slightly, depending on the dose, size of the testes and age of the animal. When the method is used on sexually immature pigs, there is an advantage to leaving some testicular function as the production of some testosterone in the testes stimulates anabolic growth. For this purpose, it is preferred that enough mineral acetate be injected to reduce the serum testosterone level to from about 70% to about 90% of an intact male, most preferably from about 75% to about 85%. At this level, there is enough testosterone to stimulate anabolic growth but not enough to effectively stimulate the development of the epididymides and other accessory glands. Injection of mineral acetate at this level also interferes with the enzymatic conversion of testosterone into androstenone, blocking the development of boar taint in the meat. This effect further tends to stimulate anabolic growth as whatever testosterone that is produced by the testes is available in the blood serum to stimulate growth, affecting carcass quality.

The method can be used on pigs on the verge of sexual maturity (i.e., pigs at about 4 to 4½ months old or about 70 kg), when knife castration is too dangerous and the animal may otherwise be sent to slaughter to prevent the development of boar taint. If a nearly sexually mature hog is treated with mineral acetate, it can be grown to a larger size without the development of boar taint or, with a smaller dose, with taint at an acceptable level in that region of the world. Even older or fully grown boars (i.e., pigs weighing 120 kg or more) can be castrated by injecting mineral acetate, either completely or to the extent necessary to reduce the boar taint to an acceptable level. In general, it is preferred that the serum testosterone level be reduced about 20% or more below that of an intact pig.

The present method can be used by stockmen with minimum changes in husbandry practices and without increasing management costs as the injection can be given when the animal is inoculated or otherwise handled. It can be used on piglets by stockmen who are accustomed to knife castrating at an early age. It can be used by stockmen who normally do not castrate and send their pigs to slaughter at 4 to 4½ months and on old boars where surgical castration is too risky. With baby pigs and sexually immature pigs, the method can be used to increase meat production either by stimulating growth or extending the period for growth and with old boars can be used to salvage meat which would otherwise be unacceptable for human consumption.

Suitable mineral acetates for use in the present invention include zinc acetate and calcium acetate. The amount of mineral acetate necessary to effect reduction of the serum testosterone level to an acceptable level (e.g., below about 20% of an intact male) depends on the weight and sexual maturity of the pig at the time of injection. Other factors include testis size, breed (i.e., genetics) and so forth. By way of non-limiting example, a dose of 50 to 100 mg in each testes has been found sufficient to reduce the serum testosterone level by more than 70% of an intact pig in two week old Yorkshire pigs, with a dose of 75 to 85 mg being preferred. A pig's testis increases in size rapidly during early stages of development and by 4 to 4½ months of age, a dose of 200 to 500 mg may be required to reduce the serum testosterone level by more than 70% of an intact pig. For older pigs or pigs with bigger testes, a dose as large as 1,000 to 2,500 mg may be required depending on the effect desired (e.g., from a serum reduction of 20% to complete castration) with injection occurring several weeks before slaughter for the boar taint to dissipate from the carcass. Summarizing the above, the size of the dose must be tailored to the size of the hog's testes, sexual maturity and the effect desired.

The mineral acetate should be delivered in solution (preferably aqueous) and in a volume that does not split the testes. This can be accomplished, for example, when the concentration of the mineral acetate salt is from about 5 to about 30% by weight. Solutions having this amount of mineral acetate have a pH in the range from about 6 to 6.8 and can be injected into the testes or epididymides without severe swelling and causing the animal discomfort. The solution may contain non-interfering amounts of pharmaceutically and physiologically acceptable bactericides, stabilizers and so forth commonly found in injectable compositions. A particularly attractive injection device is sold by Horizon Medical Inc. of Santa Ana, Calif. under the trademark UNI-JECT. A plastic bulb is pre-filled with the mineral acetate solution and attached to a disposable needle. Two syringes are needed for each hog, one for each testis, reducing the possibility for infection, but reusable syringes may also be used if the needle is properly sterilized, between animals and preferably between testes.

Injection of mineral acetate into a pig's testis has one or more of the following effects on testicular function: (a) atrophy of the seminiferous tubules, (b) scar tissue formation and atrophy in the rete testis, (c) atrophy of the coils of the head and body of the epididymis, (d) atrophy of the Leydig cells resulting in significant reduction of testosterone hormone, (e) atrophy of the seminal vesicles, prostate and Cowper's gland and (f) decrease in the blood microcirculation within the testes which results in reduction of the blood supply to the testicular tissues. As discussed above the severity of the effects depends on the dose, sexual maturity of the animal and so forth.

The following examples illustrate the invention with the exception of Example 1 which is reported for purposes of comparison.

EXAMPLE 1

Ninety-six Yorkshire sired male pigs were used to determine the effectiveness of a zinc-arginine complex for chemical castration by intratesticular injection. Four week old pigs were randomly assigned to four groups: intact male controls (IM), 50 mg injection (50I) delivered in 0.5 ml solution, 100 mg injection (100I) delivered in 1.0 ml solution and knife castrates (KC). Injections were performed by first cleaning the injection site thoroughly with isopropyl alcohol. Then a ½ inch 26 gauge was inserted near the dorsal end of the testis and run lengthwise approximately half the length of the testis. This insured that the compound was deposited as near the center of the testis as possible. During proper injection of the solution the testis swelled slightly to the touch. All pigs were returned to the sow.

Pigs were weaned at approximately six weeks of age and allowed six weeks to reach sufficient size to enter the finishing facility for the gain test. At approximately twelve weeks of age, pigs were weighed and initial blood samples were taken. One-half of the pigs from each treatment group were randomly assigned for blood collection. All pigs were weighed biweekly through week 22 and blood samples were obtained from the appropriate individuals using jugular puncture. Blood samples were kept on ice for a short period and then centrifuged to separate the plasma portion, which was frozen for future testosterone analysis.

Pigs were reared in pens of eight with two of each treatment per pen from ten weeks of age to market weight. Additionally, blood samples were collected biweekly beginning at 14 weeks. At slaughter ($104 \pm 11.4$ kg), testicular and epididymal weights were taken. Carcass data were collected and fat samples were frozen for sensory analysis. Total testicular weights (548.8, 488.7 and 408.7 g) and epididymal weights (115.0, 91.2 and 79.1 g) for IM, 50I and 100I, respectively, were reduced ($P<0.05$) in a linear dose response. Control and treated males had less average backfat (36.1, 34.0, 36.3 and 42.7 mm), less tenth rib fat depth (35.8, 32.5, 35.6 and 46.2 mm), a larger longissium area (LA) (27.5, 28.0, 27.5 and 23.8 $cm^2$), were longer (79.5, 80.0, 79.2 and 77.0 cm) and had lower dressing percentages (71.7, 71.0, 71.3 and 73.0), respectively, than KC ($P<0.05$). Additionally, 50 I pigs had less backfat than 100 I ($P<0.05$). Serum testosterone levels were reduced at 22 weeks of age for 100I when compared to IM ($P<0.05$). Additionally, there was a trend toward lower testosterone values at 20 weeks of age between 100I and the other boar groups ($P<0.10$). In sensory panel boar odor evaluation, KC samples had lower boar odor mean scores than all other groups (4.7, 6.0, 5.7 and 3.1) and IM had significantly lower scores than either 50I or 100I ($P<0.05$). Hence, treatment with zinc arginine increased boar taint even though serum testosterone was lowered.

EXAMPLE 2

Twenty-four Yorkshire, male, fifteen day-old pigs were divided into the following four groups, each of which had a littermate.

Group 1: Control
Group 2: Castrated
Group 3: Injected with 0.3 ml of 50.16 zinc acetate/testes
Group 4: Injected with 0.3 ml of 75.24 mg zinc acetate/testes The data from the study are presented in the tables below. There was no significant difference in body weight on Day 0 of the study, as shown in Table I, results at the end of the study (five months post-injection) indicated a better growth rate in the animals treated with 75.24 mg zinc acetate/testes as compared to control, castrated and animals treated with 50.16 mg zinc acetate/testes.

TABLE I

| | Average Body Weight (kg) of Pigs On Day 0 and Five Months Post-Injection | |
|---|---|---|
| GROUP | BODY WEIGHT (kg) | BODY WEIGHT (kg) FIVE MONTHS POST-INJECTION |
| Control | 4.95 | 109.69 |
| Castrated | 5.02 | 106.37 |
| 50.16 mg Zinc Acetate | 4.88 | 107.48 |
| 75.24 mg Zinc Acetate | 5.02 | 111.48 |

Reproductive organ weights decreased significantly as evidenced by the data in Table II and by photographs of reproductive organs from control boar 91-3 and boar 95-9 injected with 75.24 mg zinc acetate.

TABLE II

| | Testes Measurements (mm) At Five Months Post-Injection | | | |
|---|---|---|---|---|
| | RIGHT | | LEFT | |
| GROUP | Width | Length | Width | Length |
| Control | 65.50 | 120.17 | 65.00 | 117.67 |
| Castrated | — | — | — | — |
| 50.16 mg Zinc Acetate | 58.67 | 85.00 | 63.50 | 99.33 |
| 75.24 mg Zinc Acetate | 9.67 | 17.00 | 32.17 | 51.00 |

The decrease in reproductive organ weights corresponded to decrease in serum testosterone level as shown in Tables III–VI.

TABLE III

| | Control Serum Testosterone Level (ng/ml) | | | |
|---|---|---|---|---|
| Animal Number | 1 Month Post Injection | 2 Months Post Injection | 4 Months Post Injection | 5 Months Post Injection |
| 91-3 | 0.29 | 0.32 | 1.49 | 13.23 |
| 92-12 | 0.48 | 0.63 | 3.19 | 3.42 |
| 93-5 | 0.27 | 1.42 | 1.90 | 14.22 |
| 94-10 | 0.30 | 0.20 | 2.00 | 1.58 |
| 95-6 | 0.31 | 0.84 | 2.88 | 16.88 |
| 96-8 | 0.29 | 0.34 | 1.65 | 21.29 |
| x | 0.32 | 0.63 | 2.19 | 11.77 |
| S.D. | 0.08 | 0.45 | 0.69 | 7.73 |
| S.E. | 0.03 | 0.19 | 0.28 | 3.15 |

TABLE IV

| | Castrated Serum Testosterone Level (ng/ml) | | | |
|---|---|---|---|---|
| Animal Number | 1 Month Post Injection | 2 Months Post Injection | 4 Months Post Injection | 5 Months Post Injection |
| 91-7 | 0.17 | 0.10 | 0.09 | 0.09 |
| 92-11 | 0.09 | 0.09 | 0.08 | 0.05 |
| 93-7 | 0.11 | 0.07 | 0.08 | 0.07 |
| 94-9 | 0.11 | 0.10 | 0.09 | 0.09 |
| 95-7 | 0.11 | 0.08 | 0.07 | 0.13 |
| 96-4 | 0.12 | 0.10 | 0.08 | 0.08 |
| x | 0.12 | 0.09 | 0.08 | 0.09 |
| S.D. | 0.03 | 0.01 | 0.01 | 0.03 |
| S.E. | 0.01 | 0.01 | 0.00 | 0.01 |

TABLE V

| | Pigs Injected Intratesticularly With 50.16 mg Zinc Acetate (17.87 mg Zinc$^{++}$ in 0.3 ml Volume) Serum Testosterone Level (ng/ml) | | | |
|---|---|---|---|---|
| Animal Number | 1 Month Post Injection | 2 Months Post Injection | 4 Months Post Injection | 5 Months Post Injection |
| 91-5 | 0.16 | 0.16 | 0.33 | 1.58 |
| 92-7 | 0.17 | 0.33 | 0.36 | 1.03 |
| 93-4 | 0.18 | 0.58 | 0.72 | 3.57 |
| 95-8 | 0.15 | 0.26 | 2.23 | 7.04 |
| 96-6 | 0.15 | 1.31 | 1.31 | 12.53 |
| 96-7 | 0.21 | 0.46 | 2.32 | 8.94 |
| x | 0.17 | 0.52 | 1.21 | 5.78 |
| S.D. | 0.02 | 0.42 | 0.90 | 4.52 |
| S.E. | 0.01 | 0.17 | 0.37 | 1.85 |

TABLE VI

| | Pigs Injected Intratesticularly With 75.24 mg Zinc Acetate (26.81 mg Zinc$^{++}$ in 0.3 ml Volume) Serum Testosterone Level (ng/ml) | | | |
|---|---|---|---|---|
| Animal Number | 1 Month Post Injection | 2 Months Post Injection | 4 Months Post Injection | 5 Months Post Injection |
| 91-4 | 0.22 | 1.22 | 0.92 | 10.84** |
| 92-13 | 0.14 | 0.43 | 1.61 | 3.41*** |
| 93-3 | 0.17 | 0.16 | 0.18 | 0.20 |
| 94-8 | 0.16 | 0.19 | 0.24 | 0.35 |
| 95-9 | 0.13 | 0.11 | 0.18 | 0.25 |
| 96-3 | 0.16 | 0.44 | 0.74 | 2.90*** |
| x | 0.16 | 0.43 | 0.65 | 2.99+ / 1.42++ |
| S.D. | 0.03 | 0.41 | 0.57 | 4.10+ / 1.59++ |
| S.E. | 0.01 | 0.17 | 0.23 | 1.67+ / 1.71++ |

*Averages were calculated with and without Animal Number 91-4
+Calculated with Animal Number 91-4
++Calculated without Animal Number 91-4
**Both testes were not correctly injected
***Both testes were not correctly injected Table VII shows that, as compared to the control group, the percent change in serum testosterone level was −99.24 for the castrated group; −50.89 for the 50.16 mg zinc acetate group; and −74.60 calculated with boar 91-4 and −87.94 calculated without boar 91-4. (Zinc acetate was not effective in boar 91-4 because it was injected mistakenly into the scrotum rather than into the testes).

TABLE VII

| Percent Changes in Serum Testosterone Levels As Compared to Control Group | |
|---|---|
| Animal Group | Percent Change |
| Castrated | −99.24 |
| 50.16 mg Zinc Acetate | −50.89 |

TABLE VII-continued

Percent Changes in Serum Testosterone Levels As Compared to Control Group

| Animal Group | Percent Change | |
|---|---|---|
| 75.24 mg Zinc Acetate | −74.60** | −87.94*** |

*Calculated with and without Animal Number 91-4; both testes were not corrected injected
**Calculated with Animal Number 91-4
***Calculated without Animal Number 91-4

TABLE IX

Loin Eye Area Measurement (sq. in.) and Cuts of Meat Weights (kg)

| Group | Loin Eye Area | Ham Bone In (kg) | Ham Boneless (kg) | Loin (kg) | Picnic (kg) | Butt (kg) |
|---|---|---|---|---|---|---|
| Control | 2.25 | 9.23 | 6.54 | 7.56 | 3.98 | 3.36 |
| Castrated | 2.12 | 9.11 | 6.32 | 7.19 | 3.71 | 3.37 |
| 50.16 mg Zinc Acetate | 2.27 | 9.09 | 6.29 | 7.37 | 4.20 | 3.28 |
| 75.24 mg Zinc Acetate | 2.40 | 9.68 | 6.85 | 8.08 | 4.18 | 3.62 |

TABLE X

Meat Yields

| GROUP | Loin Eye Area (sq. in.) | % of Boneless Ham to Total Ham Weight | Ham (%) Boneless | Ham (%) Bone In | Loin (%) | Picnic (%) | Butt (%) |
|---|---|---|---|---|---|---|---|
| Control | 4.97 | 70.99 | 16.13 | 22.72 | 18.69 | 9.79 | 8.25 |
| Castrated | 4.68 | 69.28 | 15.57 | 22.47 | 17.67 | 9.18 | 8.31 |
| 50.16 mg Zinc Acetate | 5.00 | 69.37 | 15.93 | 22.95 | 18.72 | 10.49 | 8.28 |
| 75.24 mg Zinc Acetate | 5.30 | 70.75 | 15.90 | 22.49 | 18.79 | 9.75 | 8.41 |

TABLE XI

Carcass Yields

| GROUP | Final Body Weight (kg) | Hot Carcass Weight (kg) | Hot Carcass Yield (%) | Cold Carcass Right Side Weight (kg) | Cold Carcass Left Side Weight (kg) | Cold Carcass Total Weight (kg) | Cold Carcass Yield (%) |
|---|---|---|---|---|---|---|---|
| Control | 109.69 | 85.58 | 78.17 | 40.67 | 39.61 | 80.25 | 73.21 |
| Castrated | 106.37 | 83.76 | 78.80 | 40.60 | 40.14 | 80.74 | 75.97 |
| 50.16 mg Zinc Acetate | 107.50 | 82.63 | 76.76 | 39.73 | 38.52 | 78.24 | 72.71 |
| 75.24 mg Zinc Acetate | 111.51 | 89.66 | 80.41 | 43.09 | 41.84 | 84.94 | 76.17 |

EXAMPLE 3

The better growth rate of the animals treated with 50.16 mg zinc acetate and 75.24 mg zinc acetate in Example 2 was confirmed when the animals were slaughtered at the end of study. The treated animals had less fat than the castrated animals, and the loin area was highest in the group treated with 75.24 mg zinc acetate, indicative of increase in good cut of meat. The data regarding meat quality is presented in the tables below.

TABLE VIII

Backfat Measurement (Inches)

| GROUP | First Thoracic | Last Thoracic | Last Lumbar | Average Carcass Backfat | Tenth Rib |
|---|---|---|---|---|---|
| Control | 1.65 | 0.90 | 0.92 | 1.16 | 0.93 |
| Castrated | 1.73 | 1.08 | 1.08 | 1.30 | 1.13 |
| 50.16 mg Zinc Acetate | 1.88 | 0.95 | 0.85 | 1.23 | 1.04 |
| 75.24 mg Zinc Acetate | 1.77 | 1.02 | 1.00 | 1.26 | 0.98 |

EXAMPLE 4

A sample of back fat and leaf fat was taken from the treatment groups described in Example 2 and frozen. Potential panelists were screened for sensitivity to boar taint by using back fat samples obtained from control and castrated pigs. Ten sensitive panelists performed all evaluations in duplicate. There were eight sessions and each panelist monadically received six samples (in randomized sequence) followed by a 5 minute break. Then the panelist monadically received six more samples (again in a unique random sequence; these were the duplicates of the original six samples). Panelists were asked to lift the lid of the sample container, sniff the headspace above the sample and rate the perceived intensity of boar taint. They then replaced the lid and returned the sample and a ballot to the experimenter and waited at least 30 seconds for the next sample.

Prior to sniffing, the frozen samples were cut into ¼ inch cubes, placed in small plastic petri dishes, covered with the petri dish lids and returned to the freezer. On the day of a session the samples were removed from the freezer and allowed to thaw. Ambient temperature was approximately 20 C. Samples were heated in identical Tappan 900 Watt microwave ovens equipped with carrousels. The samples for each judge were heated only after the judge was seated in the evaluation booth. A single sample (petri dish) was placed in the microwave, accompanied by a container filled with 1½ cups of water. The water was used to prevent the microwave magnetron from overheating since the sample was very small and did not absorb many microwaves. The water was replaced frequently, since it would start to boil. A sample was heated at full power for 120 seconds. The sample was then immediately served to the judge. The experimenter made sure that each sample was partially melted prior to serving the sample to the judge.

The samples were scored for taint in a range from 1 to 10. The results are given in the following table.

TABLE XII

| GROUP | Scoring for Boar Taint Average Taint Score |
|---|---|
| Control | 10.39 |
| Castrated | 8.63 |
| 50.16 mg Zinc Acetate | 9.63 |
| 75.24 mg Zinc Acetate | 8.50 |

EXAMPLE 5

A sample of fat was taken from the treatment groups described in Example 2 and analyzed spectrophotometrically for skatole by a method described by A. B. Mortensen and S. E. Sorensen, Danish Meat Research Institute, presented at the 30th European Meeting of Meat Research Workers, Bristol, Sep. 9–16, 1984. The results are reported in the following table.

TABLE XIII

| GROUP | Skatole (ppm) First Assay | Second Assay |
|---|---|---|
| Control | 0.083 | 0.089 |
| Castrated | 0.043 | 0.042 |
| 50.16 mg. Zinc Acetate | 0.053 | 0.047 |
| 75.24 mg Zinc Acetate | 0.047 | 0.042 |

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

Cited Literature

Beery, K. E. and J. D. Sink. 1971. Isolation and identification of 3alpha-hydroxy-5alpha-androst-16-ene- and 5alpha-androst-16-en-3-one from porcine tissue. J. Endocrinol. 51:223.

Beery, K. E., J. D. Sink, S. Patton and J. H. Ziegler. 1971. Characterization of the swine sex odor (SSO) components in boar fat volatiles. J. Food. Sci. 36:1086.

Berger, T., K. L. Esbenshade, M. A. Diekman, T. Hoagland and J. Tuite. 1981. Influence of prepubertal consumption of zearalenone on sexual development of boars. J Anim. Sci. 53:1559.

Bierschwal, C. J. and E. F. Ebert. 1961. Clinical applications of a sclerotherapeutic agent. Vet Med. 56:323.

Bonneau, M. 1981. Endocrinological and physical aspects of boar taint. Conference Report On Boar Taint, 1981, Zeist. Livest. Prod. Sci. 8:573.

Bonneau, M. and M. Terqui. 1982. A note on the metabolism of 5alpha-androst-16-en-3-one in the young boar in vivo. Reprod. Nutr. Dev. 23:899.

Brooks, R. I. and A. M. Pearson. 1989. Odor thresholds of the $C_{19}$-Steroids responsible for boar odor in pork. Meat Sci. 24:11.

Brooks, R. I., A. M. Pearson, M. G. Hogberg, J. J. Pestka and J. I. Gray. 1986. An immunological approach for prevention of boar odor in pork. J. Anim. Sci. 62:1279.

Claus, R. 1976. Messung des Ebergeruchstoffes im Fett von Schweinen mittels eines Radioimmunotests. II. Zeitlecher Verlauf des Geruchdepotabbaues nach der kastration. Z. Tierz. Zuchtungsbiol. 93:38.

Claus, R. 1979. Pheromone bei Suagetieren unter besonderer Berucksichtigung des Ebergeruchsstoffes und seiner Beziehung zu anderen Hodensteroiden. Z. Tierphysiol. Tierernahr. 10:1.

Freeman, C. and D. S. Coffey. 1973. Sterility in male animals induced by injection of chemical agents into the vas deferens. Fertil. Steril. 24:884.

Gower, D. B. 1972. 16-unsaturated $C_{19}$ steroids. A review of their chemistry, biochimeisty and possible physiological role. J. Steroid Biochem. 3:45.

Hansson, K. E., K. Lundstrom, S. Fjelkner-Modig, and J. Persson. 1980. The importance of androstenone and skatole for boar taint. Swedish J. Agric. Res. 10:167.

Hines, R. H., J. A. Hoefer, R. A. Merkel and E. R. Miller. 1969. Influences of restricted feeding and sex upon performance and carcass quality. Michigan Swine Research Report. 99:53.

Jonsson, P. and 0. Andresen. 1979. Experience during two generations of within-lines testing, using 5alpha-androst-16-ene-3one (5alpha-androstenone) and an olfactory judgement of boar taint. Ann. Genet. Sel. Anim. 11:241.

Kluber, E. F., III, J. E. Minton, J. S. Stevenson, M. C. Hunt, D. L. Davis, T. A. Hoagland and J. L. Nelssen. 1988. Growth, carcass traits, boar odor and testicular and endocrine functions of male pigs fed a progestogen, altrenogest. J. Anim. Sci. 66:470.

Kuhlers, P. L., L. L. Christian and H. H. Lsou. 1976. Performance differences between boars and barrows taken to heavier weights. Duroc News. 50:301.

Lerche, H. 1936. Geschlechtsgeruch bei eberkastraten. Z. Fleisch. Milchhyg. 46:417.

Lundstrom, K., B. Malmfors, G. Malmfors, S. Stern, H. Petersson, A. B. Mortensen, and S. E. Sorensen. 1988. Skatole, androstenone and taint in boars fed two different diets. Livest. Prod. Sci. 18:55.

Malaviya, B., H. Chandra, and A. B. Kar. 1974. Chemical occlusion of vas deferens by quinacrine in rhesus monkeys. Indian J. Exp. Biol. 62:560.

Malmfors, B. and K. Lundstrom. 1983. Consumer reactions to boar meat: A review. Livest. Prod. Sci. 10:187.

Mortensen, A. B., C. Bejerholm, and J. K. Pedersen. 1986. Consumer test of meat from entire males, in relation to skatole in backfat. Proc. 32nd European Meeting of Meat Research Workers, Ghent, 23–26.

Patterson, R. L. S. 1968. 5alpha-androst-16-ene-3-one: Compound responsible for taint in boar fat. J. Sci. Food Agr. 19:31.

Pineda, M. H., T. J. Reimers, L. C. Faulkner, M. L. Hopwood, and G. E. Seidel. 1976. Azoospermia in dogs induced by injection of sclerosing agents into the caudae of the epididymides. Am. J. Vet. Res. 38:831.

Vold, E. 1970. Fleischproduktionseigenschaften bei Ebern und Kastraten. IV. Organoleptische und gaschromatographische Untersuchungen wasserdampfflüchtiger Stoffe des Ruckenspeckes von Ebern. Report No. 238. Institute of Animal Genetics and Breeding, NLH, Vollebekk. 25.

Walstra, P. 1984. Analytical methods for determination of boar taint. Report From the E. A. A. P. Working Group Meeting, Oct. 1984, Holbaek. Livest. Prod. Sci. 13:303.

Walstra, P. and H. Maarse. 1970. Onderzoek geslachtsgeur van mannelijke mestvarkens. I. V. 0.-Rapport C-147 and Rapport No. 2. Researchgroip Vlees en Vleeswren T. N. 0., Zeist, 30.

Willeke, H. 1980. A selection experiment against 5alpha-Androst16-en-3-one, the boar taint steriod, in adipose tissue of boars. Z. Tierzuchtg. Zuchtungsbiol., 97:86.

Williamson, E. D., R. L. S. Patterson, E. R. Buxton, K. G. Mitchell, I. G. Partridge and N. Walker. 1985. Immunization against 5alpha-androstenone in boars. Livest. Prod. Sci. 12:251.

Wood, J. D. and J. E. Riley. 1982. Comparison of boars and castrates for bacon production. 1. Growth data, and carcass joint composition. Anim. Prod. 35:55.

Yokoyama, M. T. and J. R. Carlson. 1979. Microbial metabolites of tryptophan in the intestinal tract with special reference to skatole. Am. J. Clin. Nutr. 32:173.

What is claimed:

1. A method of chemically castrating a pig in a manner that stimulates anabolic growth comparable or better than an intact pig while reducing boar taint in the pig's carcass comprising injecting a solution consisting essentially of zinc acetate, calcium acetate or mixtures thereof into each testes or epididymis in an amount effective to reduce the pig's serum testosterone level below that of an intact pig.

2. The method of claim 1 wherein the serum testosterone level is reduced about 20% or more below that of an intact pig.

3. The method of claim 1 wherein the serum testosterone level is reduced about 70% to about 90% below that of an intact pig.

4. The method of claim 3 wherein the mineral acetate is zinc acetate and the solution has a pH in the range from about 6 to about 6.8.

5. The method of claim 3 wherein between about 50 and 2,500 mg of zinc acetate is injected into each testis depending on the size of the testis, sexual maturity of the pig and effect desired.

* * * * *